(12) United States Patent
Bauer et al.

(10) Patent No.: US 6,752,986 B2
(45) Date of Patent: Jun. 22, 2004

(54) COMPOSITION AND METHODS FOR AFFECTING METALLOCORRINOID UPTAKE

(75) Inventors: Joseph A. Bauer, Akron, OH (US); Daniel J. Lindner, Shaker Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 240 days.

(21) Appl. No.: 09/864,747

(22) Filed: May 24, 2001

(65) Prior Publication Data

US 2003/0161812 A1 Aug. 28, 2003

(51) Int. Cl.[7] .................. A61K 38/21; A61K 38/00; A61K 31/70; C07K 17/00; C07K 23/00
(52) U.S. Cl. ..................... 424/85.6; 514/2; 514/52; 424/85.4; 530/351; 536/26.4
(58) Field of Search ............... 424/85.4, 85.6; 514/2, 52; 530/351; 536/26.4

(56) References Cited

U.S. PATENT DOCUMENTS

| | | | |
|---|---|---|---|
| 5,698,232 A | * 12/1997 | Kanemaru et al. | ......... 424/85.4 |
| 5,936,082 A | 8/1999 | Bauer | |
| 6,096,290 A | 8/2000 | Collins et al. | |
| 6,183,723 B1 | 2/2001 | Seetharam et al. | |

FOREIGN PATENT DOCUMENTS

EP          0 220 030 B1     10/1986

OTHER PUBLICATIONS

Medinica et al., Blood, 1995, vol. 86, suppl. 1, p. 850B.*
The Merck Index, Merck and Co., 1989, p. 1577.*
One–A–Day 50 Plus Multivitamins, Bayer Corporation.*
Nutri Mega Multivitamins, American Health Corporation.*
Dinarello, 2000, Chest, vol. 118, pp. 503–508.*
Amagasaki, T., Green, R. & Jacobsen, D.W. Expression of transcobalamin II receptors by human leukemia K562 and HL–60 cells. Blood 76, 1380–6. (1990).
Bauer, J.A. Synthesis, characterization and nitric oxide release profile of nitrosylcobalamin: a potential chemotherapeutic agent. Anticancer Drugs 9, 239–44. (1998).
Begley, J.A. & Hall, C.A. Measurement of vitamin B12–binding proteins of plasma. I. Technique. Blood 45, 281–6. (1975).
Begley, J.A. & Hall, C.A. Measurement of vitamin B12–binding proteins of plasma. II. Interpretation of patterns in disease. Blood 45, 287–93. (1975).
Blomquist, L., Flodh, H. & Ullberg, S. Uptake of labelled vitamin B 12 and 4–iodophenylalanine in some tumors of mice. Experientia 25, 294–6. (1969).
Bose, S., Seetharam, S., Hammond, T.G. & Seetharam, B. Regulation of expression of transcobalamin II receptor in the rat. Biochem J 310, 923–9. (1995).
Bose, S. Seetharam, S. & Seetharam, B. Membrane expression and interactions of human transcobalamin II receptor. J Biol Chem 270, 8152–7. (1995).
Bose, S., et al. In vitro and in vivo inactivation of transcobalamin II receptor by its antiserum. J. Biol Chem 271, 4195–200. (1996).
Bose, S., Feix, J., Seetharam, S. & Seetharam, B. Dimerization of transcobalamin II receptor. Requirement of a structurally ordered lipid bilayer. J Biol Chem 271, 11718–25. (1996).
Bose, S. & Seetharam, B. Effect of disulfide bonds of transcobalamin II receptor on its activity and basolateral targeting in human intestinal epithelial Caco–2 cells. J Biol Chem 272, 20920–8. (1997).
Bose, S. Seetharam, S., Dahms, N.M. & Seetharam, B. Bipolar functional expression of transcobalamin II receptor in human intestinal epithelial Caco–2 cells. J Biol Chem 272, 3538–43. (1997).
Bose, S. & Seetharam, B. Purification, membrance expression, and interactions of trasncobalamin II receptor, Methods Enzymol 281, 281–9. (1997).
Carmel, R. Extreme elevation of serum transcobalamin I in patients with metastatic cancer. N Engl J Med 292, 282–4. (1975).
Chlichlia, K. et al. Caspase activation is required for nitric oxide–mediated, CD95 (APO–1/Fas)—dependent and independent apoptosis in human neoplastic lymphoid cells, Blood 91, 4311–20. (1998).
Collins, D.A. et al. Biodistribution of radiolabeled adenosylcobalamin in patients diagnosed with various malignancies. Mayo Clin Proc 75, 568–80. (2000).
Cooper, B.A.e.a. Selectrive uptake of specifically bound cobalt–58 vitamin B12 by human and mouse tumor cells. Nature 191, 393–395. (1961).
Cooperman, J.e.a. Distribution of radioactive and nonradioactive vitamin B12 in the dog. Journal of Biological Chemistry 235, 191–194. (1960).

(List continued on next page.)

*Primary Examiner*—Yvonne Eyler
*Assistant Examiner*—Janet L. Andres
(74) *Attorney, Agent, or Firm*—Pepper Hamilton LLP

(57) ABSTRACT

The present invention is directed to compositions and methods for affecting metallocorrinoid uptake. The compositions and methods of the present invention are particularly useful in enhancing the uptake or availability of biologically active metallocorrinoids (e.g. cobalamin and its analogs). The present invention is particularly useful in the treatment or prevention of conditions that result from low expression or activity of proteins involved in the processing of metallocorrinoids, as well as in conditions which would benefit from enhanced uptake or availability of cobalamin or its biologically active analogs of cobalamin (e.g. cobalamin drug conjugates).

28 Claims, 8 Drawing Sheets

(2 of 8 Drawing Sheet(s) Filed in Color)

OTHER PUBLICATIONS

Cooperman, J.M. Distribution of radioactive and nonradioactive vitamin B12 in normal and malignant tissues of an infant with neuroblastoma. Cancer Res 32, 167–72. (1972).

Digirolamo, P.M. & Huennekens, F.M. Transport of vitamin B12 into mouse leukemia cells. Arch Biochem Biophys 168, 386–93. (1975).

Flodh, H. & Ullberg, S. Accumulation of labelled vitamin B12 in some transplanted tumours. Int J Cancer 3, 694–9. (1968).

Gross, S.S. & Wolin, M.S. Nitric oxide: pathophysiological mechanisms. Annu Rev Physiol 57, 737–69. (1995).

Huennekens, F.M., Digirolamo, P.M., Fujii, K., Jacobsen, D.W. & Vitols, K.S. B12—dependent methionine synthetase as a potential target for cancer chemotherapy, Adv Enzyme Regul 14, 187–205. (1976).

Jensen, H.S., Gimsing, P., Pedersen, F. & Hippe, E. Transcobalamin II as an indicator of activity in metastatic renal adenocarcinoma. Cancer 52, 1700–4. (1983).

Lindemans, J. et al. Uptake of transcobalamin II–bound cobalamin by HL–60 cells: effects of differentiation induction. Exp Cell Res 184, 449–60. (1989).

McLean, G.R. et al. Cobalamin analogues modulate the growth of leukemia cells in vitro. Cancer Res 57, 4015–22. (1997).

McLean, G.R. et al. Antibodies to transcobalamin II block in vitro proliferation of leukemic cells. Blood 89, 235–42. (1997).

McLean, G.R., Williams, M.J., Woodhouse, C.S. & Ziltener, H.J. Transcobalamin II and in vitro proliferation of leukemic cells. Leuk Lymphoma 30, 101–9. (1998).

Pathare, P.M. et al. Synthesis of cobalamin–biotin conjugates that vary in the position of cobalamin coupling. Evaluation of cobalamin derivative binding to transcobalamin II. Bioconjug Chem 7, 217–32. (1996).

Quadros, E.V., Sai, P. & Rothenberg, S.P. Functional human transcobalamin II isoproteins are secreted by insect cells using the baculovirus expression system. Blood 81, 1239–45. (1993).

Quadros, E.V. & Jacobsen, D.W. The dynamics of cobalamin utilization in L–1210 mouse leukemia cells: a model of cellular cobalamin metabolism. Biochim Biophys Acta 1244, 395–403. (1995).

Rabinowitz, R., Rachmilewitz, B., Rachmilewitz, M. & Schlesinger, M. Production of transcobalamin II by various murine and human cells in culture. Isr J Med Sci 18, 740–5, (1982).

Rigby, C.a.B., M. Experimental study of the relationship between vitamin B12 and two animal tumor systems. Brit. J. Cancer 17, 90–99. (1963).

Ryel, E.M., Meyer, L.M. & Gams, R.A. Uptake and subcellular distribution of vitamin B12 in mouse L1210 leukemic lymphoblasts. Blood 44, 427–33. (1974).

Seetharam, B., Bose, S. & Li, N. Cellular import of cobalamin (Vitamin B–12). J Nutr 129, 1761–4. (1999).

Seetharam, B. & Li, N. Transcobalamin II and its cell surface receptor. Vitam Horm 59, 337–66. (2000).

Shimizu, N., Hamazoe, R., Kanayama, H., Maeta, M. & Koga, S. Experimental study of antitumor effect of methyl–B12. Oncology 44, 169–73. (1987).

Takahashi, K., Tavassoli, M. & Jacobsen, D.W. Receptor binding and internalization of immobolized transcobalamin II by mouse leukemia cells. Nature 288, 713–5, (1980).

Tsao, C.S., Miyashita, K. & Young, M. Cytotoxic activity of cobalamin in cultured malignant and nonmalignant cells. Pathobiology 58, 292–6. (1990).

Tsao, C.S. & Myashita, K. Influence of cobalamin on the survival of mice bearing ascites tumor. Pathbiology 61, 104–8. (1993).

Waxman, S. & Gilbert, H.S. Characteristics of a novel serum vitamin–B12–binding protein associated with hepatocellular cacinoma. Br J Haematol 27, 229–39. (1974).

Zittoun, J., Zittoun, R. Marquet, J. & Sultan, C. The three transcobalamins in myeloproliferative disorders and acute leukemia. Br J Haematol 31, 287–98. (1975).

* cited by examiner

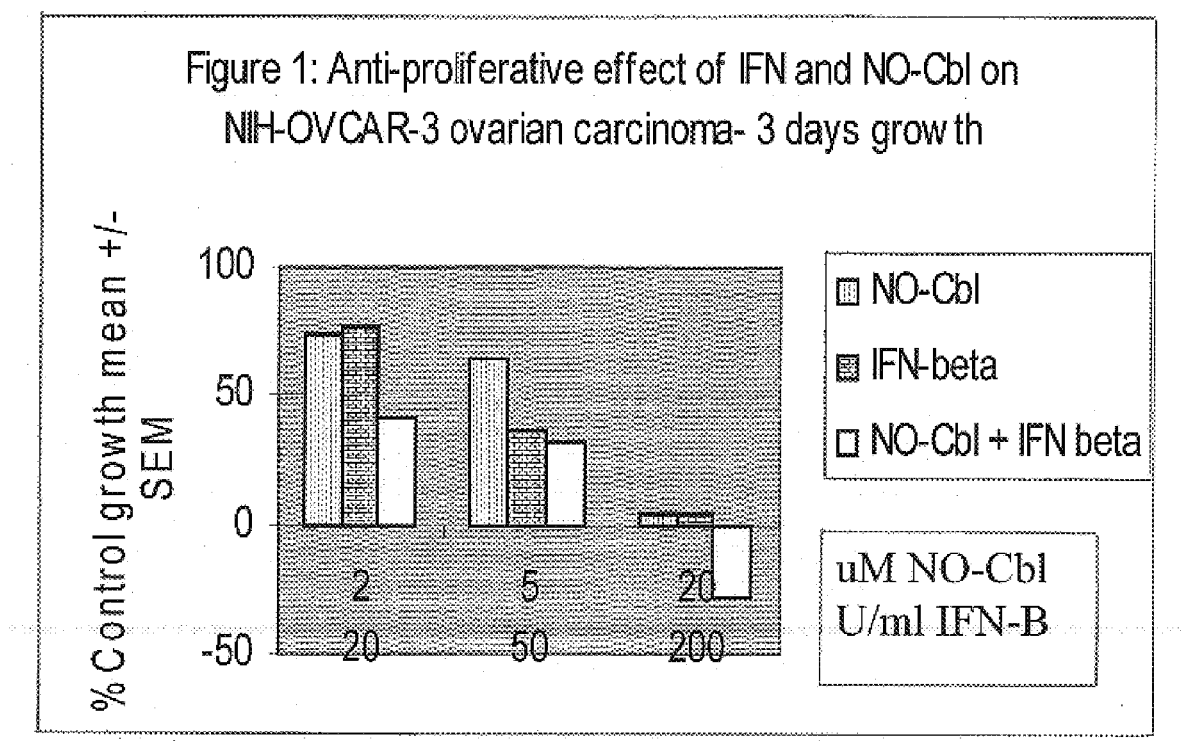

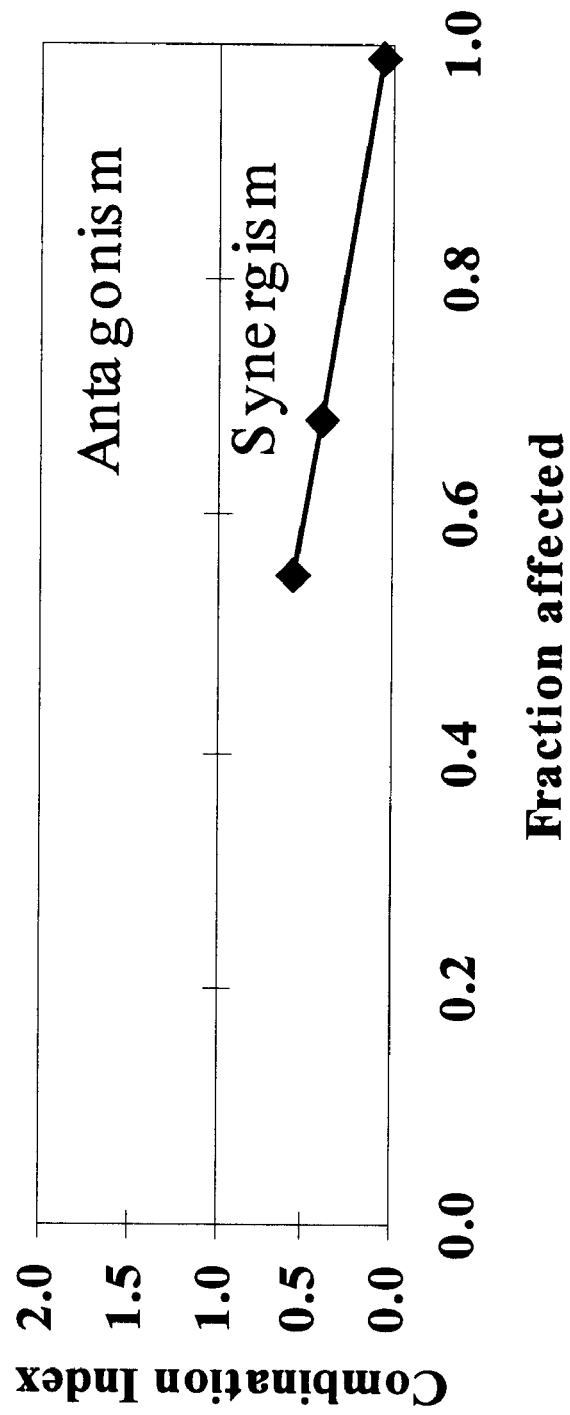

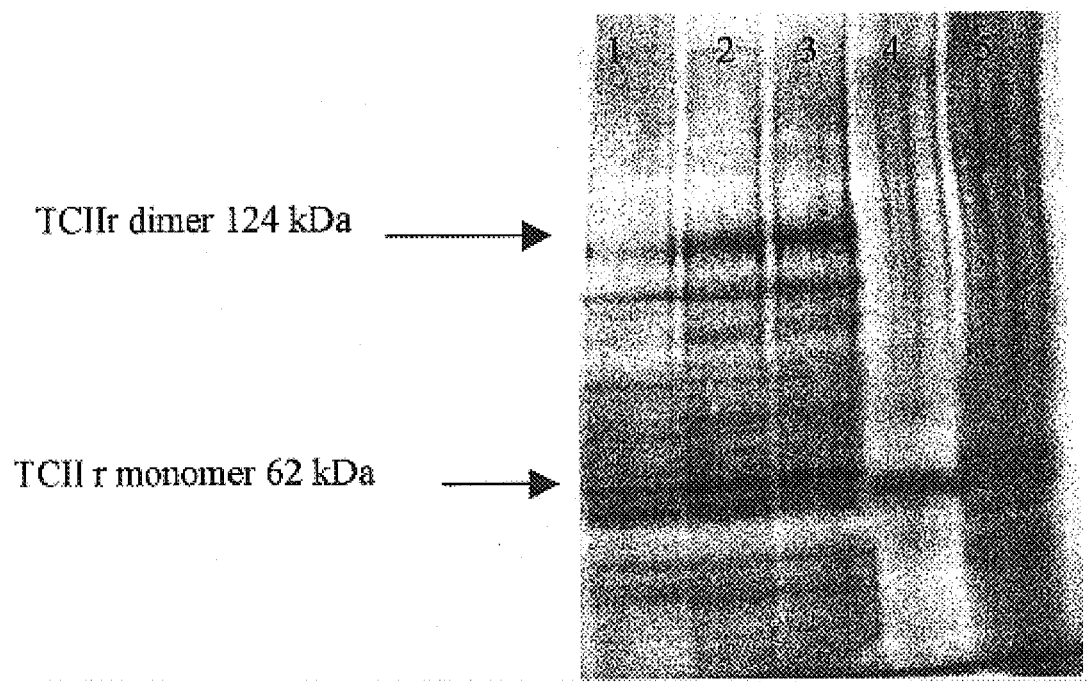
Figure 3: TCIIr Western Blot of NIH-OVCAR-3 cell extracts
TCIIr dimer 124 kDa →
TCII r monomer 62 kDa →

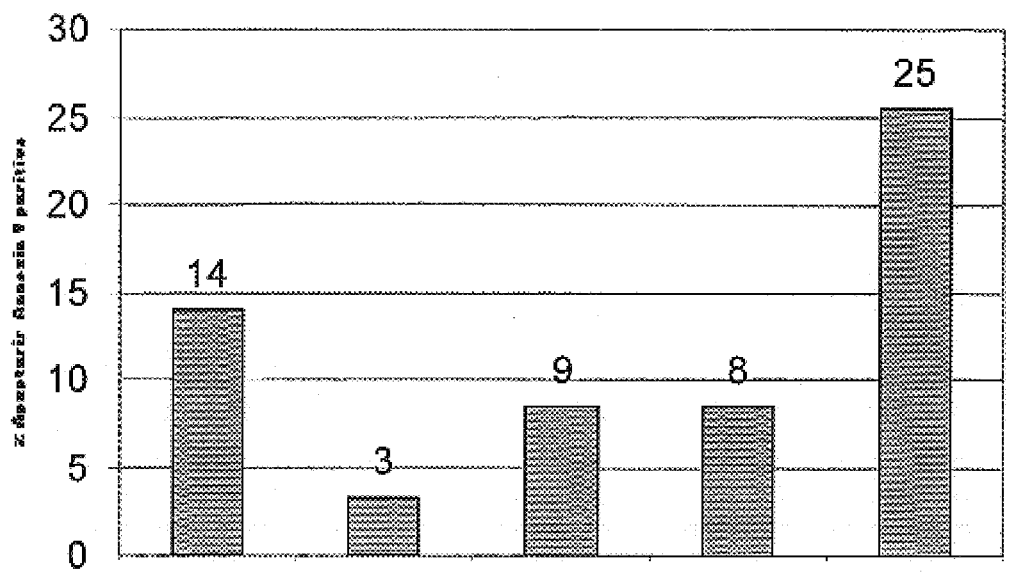

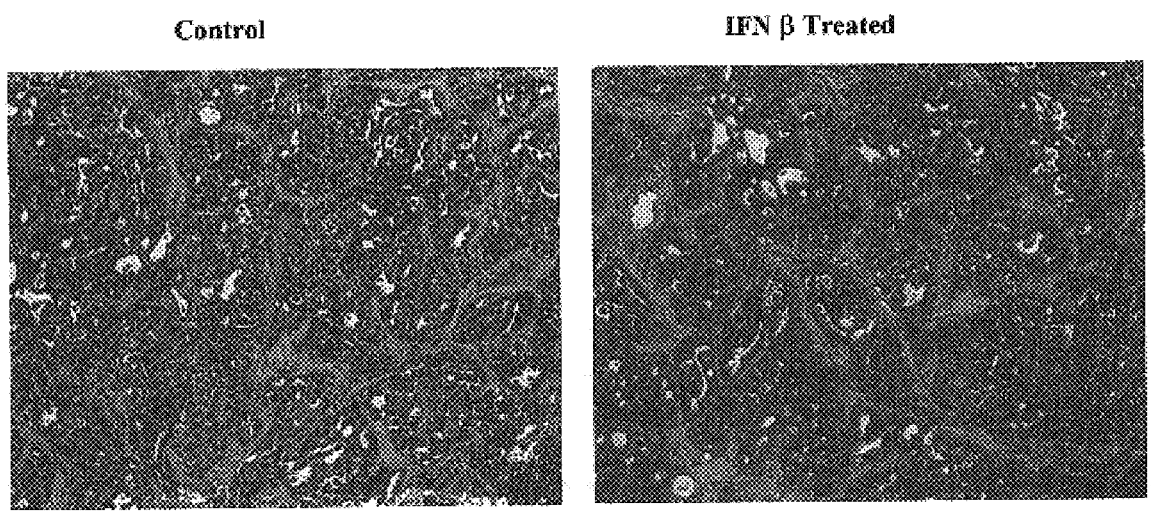
Figure 5: TCIIr up-regulation by IFN-β in NIH-OVCAR-3 tumors

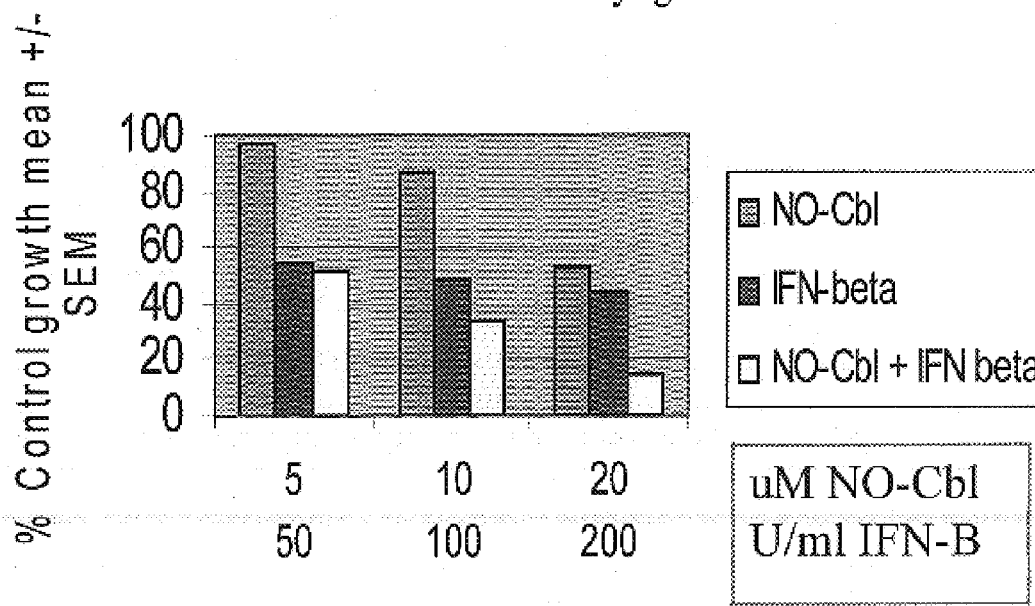

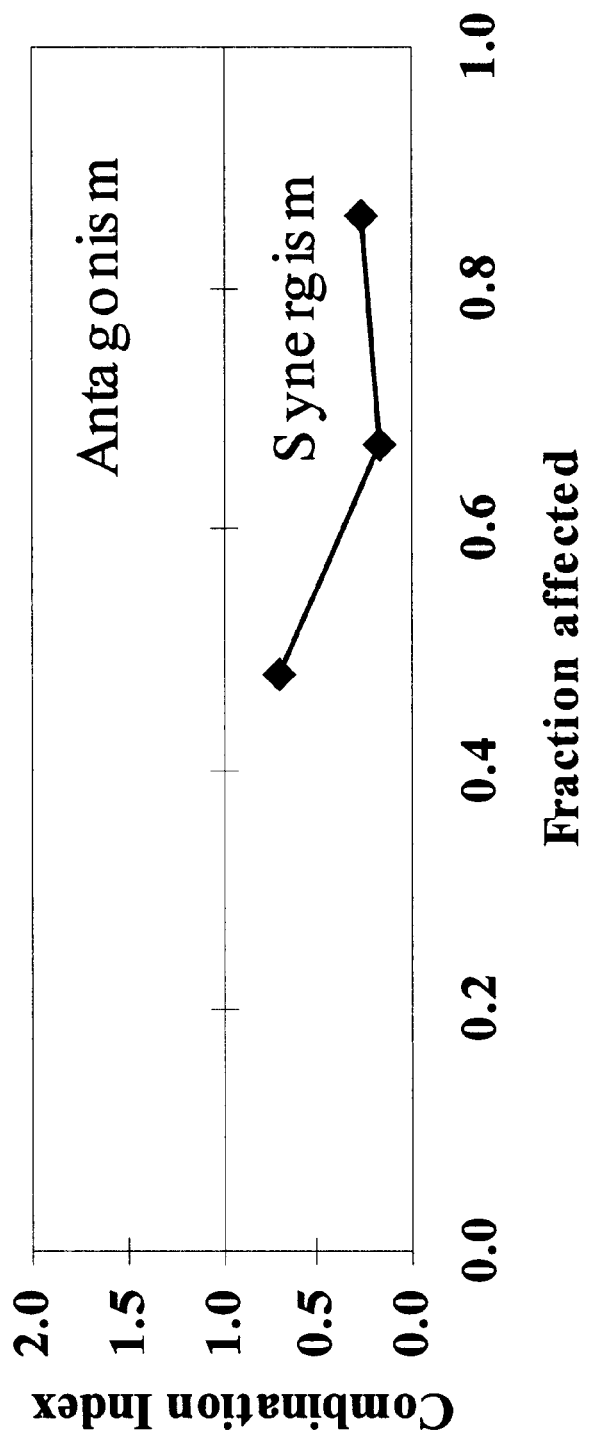
Figure 7: WM9 Median Effect Analysis

Figure 8: TCIIr Up-regulation by IFN-β in WM9 tumors
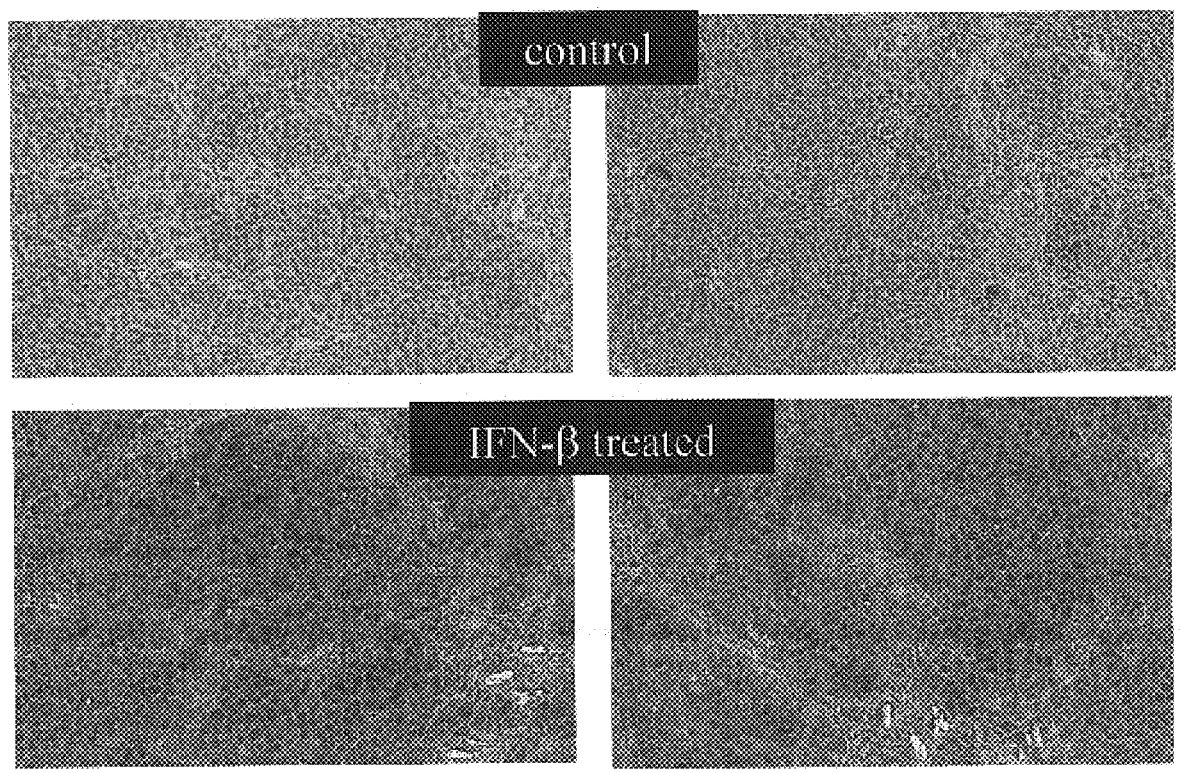

COMPOSITION AND METHODS FOR AFFECTING METALLOCORRINOID UPTAKE

BACKGROUND OF THE INVENTION

Metallocorrinoids are corrin rings with a metal-atom center, such as Co, Fe, Ni, or Mn. A corrin ring is four reduced pyrrole rings linked together A subclass of naturally occurring metallocorrinoids is known as cobalamin, that is, a cobalt-centered corrin ring. Naturally occurring vitamin $B_{12}$, for example, is a cobalamin.

Vitamin $B_{12}$ compounds are known to have many biological functions. They are required by the enzyme methionine synthase, for example, which is involved in the production of DNA. Pregnant women need increased amounts of vitamin $B_{12}$ which is involved in the production of red blood cells. It is also believed that vitamin $B_{12}$ enhances the effects of other vitamins and nutrients in tissue repair. Lack of vitamin $B_{12}$ leads to megaloblastic anemia (characterized by large and immature red blood cells) and neuropathy in man with insidious onset of symptoms. These symptoms include weakness, tiredness, breathlessness (dyspnea) on exertion, tingling and numbness (paresthesia), sore tongue (glossitis), loss of appetite and weight, loss of sense of taste and smell, impotence, psychiatric disturbances (such as irritability, memory impairment, mild depression, hallucinations) and severe anemia (which may lead to signs of cardiac dysfunction). Deficiency of vitamin $B_{12}$ leads to defective DNA synthesis in cells; tissues most affected are those with the greatest rate of cell turnover, e.g. the haematopoietic system. In small children Cbl deficiency can result in developmental delay, hematological disorders, and neurological disorders. There may be irreversible damage to the nervous system with specific demyelination of the spinal cord.

Increased availability of vitamin $B_{12}$, on the other hand, appears to have a very beneficial effect. Cbl analogs and cobalamin drug conjugates have been shown to inhibit the growth of leukemia cells by possibly deactivating methionine synthase, thus preventing DNA synthesis. The cobalamins that are analogous to vitamin $B_{12}$ compounds would appear to be potential therapeutic agents. These include hydroxocobalamin, cyanocobalamin, nitrocobalamin, mehtylcobalamin, and 5'-deoxyadenocobalamin, as well as nitrosylcobalamin.

All forms of vitamin $B_{12}$ (adenosyl-, cyano-, hydroxo-, or methylcobalamin) are bound by the transport proteins intrinsic factor and transcobalamin II, to be biologically active. Those transport proteins involved in the uptake of vitamin $B_{12}$ are referred to herein as cobalamin binding proteins. Specifically, gastrointestinal absorption of vitamin $B_{12}$ relies upon the intrinsic factor-vitamin $B_{12}$ complex being bound by the intrinsic factor receptors in the terminal ileum. Likewise, intravascular transport and subsequent cellular uptake of vitamin $B_{12}$ throughout the body is dependent upon transcobalamin II and the cell membrane transcobalamin II receptors, respectively. After the transcobalamin II-vitamin $B_{12}$ complex has been internalized, the transport protein undergoes lysozymal degradation, which releases vitamin $B_{12}$ into the cytoplasm.

Cellular utilization of Cbl is preceded by two important receptor-mediated endocytic events. First, the dietary Cbl bound to gastric intrinsic factor (IF), a 50-kDa glycoprotein, is transported across the absorptive enterocyte via an intrinsic factor-cobalamin receptor that is expressed exclusively in the apical or the luminal membranes. The plasma transport of cobalamin to tissues/cells appears to occur via transporter transcobalamin II (TC II), by receptor-mediated endocytosis via transcobalamin II-receptor (TC II-R). Intracellularly released Cbl is then converted to its biologically active forms, (e.g. methyl-Cbl and 5'-deoxyadenosyl-Cbl) which are utilized by the cytoplasmic enzyme methionine synthase (MS) and mitochondrial at enzyme methylmalonyl-CoA mutase (MMCM), respectively. MS activity is required for folate metabolism and DNA synthesis and presents a promising target to block cell proliferation. TCII and serum Cbl levels are both increased in hepatocarcinomas and leukemias. TCII has been identified as an acute phase reactant in autoimmune disorders and infection. Several studies have shown that high levels of Cbl inhibited L1210, P388D1, CCRF-CEM, and NCTC929 cell proliferation. This is likely due to the activation of an autoimmune response.

Recent studies have shown that TC II-R is expressed as a non-covalent homodimer of molecular mass of 124 kDa in tissue plasma membranes of human, rat, and rabbit. A comprehensive review of transcobalamin II, the transcobalamin II receptor, and the uptake of vitamin $B_{12}$ is provided in "Transcobalamin II and Its Cell Surface Receptor Vitamins and Hormones", *Vitamins and Hormones*, Vol. 59, pgs. 337–366 (2000) which is incorporated herein in its entirety by reference thereto. Plasma membrane expression of TC II-R appears important for the tissue/cellular uptake of Cbl since its functional inactivation in vivo by its circulatory antiserum results in intracellular deficiency of Cbl. This intracellular deficiency in Cbl results in the development of Cbl deficiency of the animal as a whole.

The utilization of vitamin $B_{12}$ as a delivery vehicle is known art. The art describes an oral delivery system that delivers active substances (hormones, bio-active peptides or therapeutic agents) by binding these agents to cobalamin or an analog thereof.

U.S. Pat. No. 5,936,082, which is hereby incorporated by reference in its entirety, for example, describes the therapeutic effectiveness of vitamin $B_{12}$ based compounds. Nitrosylcobalamin (NO-Cbl), in particular, was evaluated for its chemotherapeutic effect. In five human hematological and eight solid tumor cell lines, NO-Cbl exhibited an $ID_{50}$ that was 5–100 fold lower in tumor cell lines compared to benign cells (fibroblasts and endothelial cells). When oxidized from NO-Cbl, the NO free radical functions in a number of capacities. NO is involved in vasodilation, and is known to contribute to increased oxidative stress, inhibition of cellular metabolism and induction of DNA damage leading to apoptosis and/or necrosis.

Radiolabelled vitamin $B_{12}$ analogs have also been described in the art as useful in vivo imaging agents. For example, U.S. Pat. No. 6,096,290, which is hereby incorporated herein in its entirety by reference thereto, describes the use of radiolabelled vitamin $B_{12}$ analogs as in vivo tumor imaging agents.

U.S. Pat. No. 6,183,723, which is also incorporated herein by reference in its entirety, describes certain other cobalamin-drug conjugates.

SUMMARY OF THE INVENTION

The multiple components of Cbl uptake, enzymes, co-factors, and transport systems present several points of attack for the therapeutic delivery of cobalamins. As is described herein, the interrelationship of TCII-R and cytokines make this an attractive target for the therapeutic delivery of biologically active metallocorrinoids. Cytokines, in particular interferon β, are shown to enhance the uptake or activity of biologically active metallocorrinoids, including vitamin $B_{12}$ analogs, homologs, and derivatives.

Vitamin $B_{12}$ analogs can be synthesized in a number of ways. In addition to conjugation of the side chains of the corrin ring, conjugation to the Cbl moiety can also be made, as can conjugation to the ribose moiety, phosphate moiety, and to the benzimidazole moiety. The conjugating agent and the drug to be conjugated depend upon the type of Cbl group that is modified and the nature of the drug. One of skill in the art would understand how to adapt the conjugation method to the particular Cbl group and drug to be coupled.

Preferred methods of attaching the drug to the Cbl molecule include conjugation to Cbl via biotin. Biotin is conjugated to either the propionamide or the acetamide side chains of the corrin ring of the Cbl molecule. The initial biotin-Cbl complex can be prepared according to Pathre, et al (Pathre, P.M., et al., "Synthesis of Cobalamin-Biotin conjugates that vary in the position in cobalamin coupling, Evaluation of cobalamin derivative binding to transcobalamin II," incorporated by reference). Vitamin $B_{12}$ is commercially available in its most stable form as cyanocobalamin from Sigma Chemical (St. Louis, Mo.).

One may most easily obtain transcobalamin II in the following manner: transcobalamin II cDNA is available in the laboratories of Drs. Seetharam (Medical college of Wisconsin) and Rothenberg (VA-Hospital, New York) TC II cDNA can be expressed in a Baculovirus system to make a large amount of functionally active TC II protein (see Quadros, E. V., et al., Blood 81:1239–1245, 1993). One of skill in the art would be able to reproduce the TC II cDNA. The antibodies to TCII-R were obtained through the laboratory of Dr. Bellur Seetharam, Med. College of WI.

One way to make cobalamin drug conjugates is through genetic engineering. In this method, a DNA sequence encoding TC II and the peptide drug may be expressed as one chimeric molecule. For example, it is possible to generate a chimeric construct using the full-length TC II cDNA and the cDNA for a peptide drug (e.g. insulin). The chimeric construct can then be expressed to produce a fusion protein consisting of the TC II-peptide drug. Following synthesis, the chimeric protein should be tested for both TC II activity and drug activity. Cobalamin can then be allowed to bind to this chimeric protein and used for therapy.

The observation that a cytokine (i.e. an interferon such as interferon-β) upregulates or enhances the activity of the TCII-R provides a basis for a number of embodiments of the present invention.

One embodiment of the present invention is a method for increasing cobalamin-binding protein activity in a subject in order to treat a condition favorably affected by an increase in said cobalamin-binding activity, said method comprising the step of administering to a subject in need of such treatment a cytokine in an amount effective to increase cobalamin-binding activity in the subject. This method may further include the step of administering a vitamin $B_{12}$ analog (which may be a naturally occurring vitamin $B_{12}$ analog), nitrosylcobalamin or other suitable vitamin $B_{12}$ drug conjugate. In this embodiment, the cytokine may be administered prior, simultaneously, or consecutively with the vitamin $B_{12}$ analog. The cytokine and/or vitamin $B_{12}$ analog may be administered prophylactically or acutely. The increased cobalamin binding protein activity is preferably TCII-R activity. The cytokine is preferably an interferon such as interferon-β.

Another embodiment of the present invention is a composition that is comprised of a metallocorrinoid and a cytokine. It is preferable that the metallocorrinoid be a vitamin $B_{12}$ analog, homolog, derivative or simply vitamin $B_{12}$. This is particularly useful when there is a deficiency in vitamin $B_{12}$ or if the vitamin $B_{12}$ analog includes a drug conjugated thereto. It is particularly preferable that the vitamin $B_{12}$ analog be a nitrosylcobalamin, but it may also be others known in the art, (e.g. hydroxocobalamin, cyanocobalamin, and methylcobalamin and 5' deoxyadenocobalamin or radiolabelled cobalamin derivatives). The composition in accordance with this embodiment of the invention may also include a pharmaceutical carrier. It is preferable that the cytokine be an interferon, and more particularly interferon-β.

Another embodiment of the present invention is a therapeutic composition comprising a cobalamin or cobalamin drug conjugate and a cytokine such as interferon-β. In this embodiment, the therapeutic composition may also further comprise a pharmaceutical carrier. This is a particular advantageous embodiment when the cobalamin drug conjugate is designed for a specific aim in mind. Nitrosylcobalamin is just one cobalamin drug conjugate, and other drug conjugates may be selected from the group consisting of hydroxocobalamin, cyanocobalamin, methylcobalamin, and 5' deoxyadenocobalamin, radiolabelled cobalamin, or other cobalamin and drug conjugate. This embodiment is particular useful in the treatment of diseases where the delivery of a therapeutic agent via a cobalamin delivery mechanism would be beneficial.

Another embodiment of the present invention is a method of enhancing uptake or activity of a metallocorrinoid comprised of administering a cytokine. It is preferable that the metallocorrinoid be a vitamin $B_{12}$ or a vitamin $B_{12}$ analog, homolog, or derivative. In this method it is preferable that the cytokine is an interferon, and more preferably that the interferon be interferon-β.

Another embodiment of the present invention is a method of enhancing cellular uptake of a metallocorrinoid comprising the step of contacting a cell with a cytokine, particularly where the step of contacting a cell with a cytokine occurs through induction of cytokine. In this embodiment, it is preferable that the metallocorrinoid is vitamin $B_{12}$ or a vitamin $B_{12}$ analog. As in other embodiments, the vitamin $B_{12}$ analog may he any suitable vitamin $B_{12}$ analog, homolog or derivatives such as a cobalamin drug conjugate. In this embodiment it is preferable that the cytokine is an interferon, particularly interferon-β.

Another embodiment of the present invention is a method of treating a patient comprising the steps of inducing cytokine production; and administering a metallocorrinoid. The step of inducing cytokine production may include administering a cytokine, or administering an agent as is known in the art to stimulate cytokine expression or production. The metallocorrinoid of this embodiment may be vitamin $B_{12}$ or a vitamin $B_{12}$ analog, homolog or derivative such as a cobalamin drug conjugate. The cytokine is preferably an interferon, more preferably interferon-β.

Yet another embodiment of the present invention is a method of enhancing bio-availability of a metallocorrinoid, comprising the step of administering interferon-β alone or in combination with a metallocorrinoid.

Yet another embodiment of the present invention is a method of treating a subject to increase TCII-R activity in a cell comprising the step of administering to a subject in need of such treatment a cytokine to increase TCII-R activity in an amount effective to increase TCII-R activity in said cell. In this embodiment, it is preferable that the subject be cobalamin deficient. Another application of this embodiment is wherein the amount is sufficient to increase TCII-R activity above normal baseline levels. Preferably, this method may also be useful when the subject has an abnormally low level of TCII-R activity. This method preferably includes the step of co-administering a substrate (or ligand) of TCII-R, wherein the substrate of TCII-R is a cobalamin based compound (e.g. cobalamin or a cobalamin drug conjugate). The cobalamin drug conjugate is preferably nitrosylcobalamin, but may be any suitable cobalamin drug conjugate such as those known in the art.

Yet another embodiment of the present invention is a method of treating cancer comprised of administering a cytokine (e.g. interferon $\beta$) to enhance the uptake or increase the availability of cobalamin analogs, homologs, or derivatives. This can be done either alone or in combination with the cobalamin analog, homolog, or derivative.

Another embodiment of the present invention is a method of imaging tissue or cells through enhanced uptake of radiolabelled vitamin $B_{12}$ analogs, homologs or derivatives via administration of a cytokine such as interferon $\beta$.

Additional aspects and applications of the present invention will become apparent to the skilled artisan upon consideration of the detailed description of the invention, which follows.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

FIG. 1 is a bar graph illustrating the anti-proliferative effect of a cytokine (i.e. an interferon) and NO-Cbl on NIH-OVCAR-3 ovarian carcinoma;

FIG. 2 is a graph illustrating a median effect analysis in accordance with the present invention;

FIG. 3 is a western blot analysis performed on extracts from ovarian carcinomas according to the present invention;

FIG. 4 illustrates a bar graph of a flow cytometric analysis of Annexin V positive cells;

FIG. 5 are stained cells illustrating up-regulated TCII-R in control and IFN-$\beta$ in NIH-OVCAR-3 treated samples;

FIG. 6 is a bar graph illustrating the anti-proliferative effect of a cytokine (i.e. interferon) and NO-Cbl on WM9 melanoma;

FIG. 7 is a graph illustrating a median effect analysis on WM9 human melanoma cells;

FIG. 8 depicts treated and untreated WM9 tumor cells in accordance with the present invention.

DETAILED DESCRIPTION OF THE INVENTION

While not wishing to be bound by theory, it appears that the uptake of metallocorrinoids such as vitamin $B_{12}$, NO-Cbl or other vitamin $B_{12}$-based compounds, is dependent upon the TCII receptor, specific for vitamin $B_{12}$. Because the TCII-R plays a central role in determining metallocorrinoid activity, the relationship between TCII-R and cytokines (e.g., interferons ("IFNs")) was evaluated. IFNs upregulate the expression of cell surface markers HLA-I, HLA-II, $\beta$2 microglobulin, and tumor associated antigens such as CEA and CA125.

The present invention provides for an increase in receptor or receptor activity responsible for the uptake of vitamin $B_{12}$ derived compounds. The administration of cytokines, particularly interferons such as IFN-$\beta$, appears to enhance the activity of TCII-R. Administering these cytokines prior to or concurrently with vitamin $B_{12}$-based compounds increases the delivery of the vitamin $B_{12}$-based compounds and like metallocorrinoids.

Increased activity (e.g. TCII-R activity) can be accomplished in a number of different ways. For example, an increase in the amount of protein or an increase in the activity of the protein (while maintaining a constant level of the protein) can result in increased "activity". An increase in the amount of protein available can result from increased transcription of the gene, increased stability of the mRNA or a decrease in protein degradation.

The present invention, by causing an increase in Cbl-binding (e.g. TCII-R) activity, permits not only the re-establishment of normal base-line levels of Cbl-binding activity, but also allows increasing such activity above normal base-line levels. Normal base-line levels are the amounts of activity in a normal control group, controlled for age and having no symptoms that would indicate alteration of Cbl-binding activity. The actual base line level will depend upon the particular age group selected and the particular measure employed to assay. When using the cytokines of the present invention not only can normal base-line levels be restored, but abnormal activity can also be increased desirably far above normal base-line levels of TCII-R binding activity. Thus, "increasing activity" means any increase in Cbl-binding protein or cobalamin uptake in the subject resulting from the treatment, according to the invention, including, but not limited to, such activity as would be sufficient to restore normal base-line levels, and such activity as would be sufficient to elevate the activity above normal base-line levels.

In one embodiment of the invention the increase in activity of the Cbl-binding activity is cytokine induced. Cytokines are soluble polypeptides produced by a wide variety of cells. Cytokines control gene activation and cell surface molecule expression. In what follows, the term "cytokine" incorporates families of endogenous molecules of various denominations: lymphokines, monokines, interleukins, interferons, colonization factors and growth factors and peptides. The known cytokines are in particular interferon-$\alpha$ (IFN-$\alpha$), interferon-$\beta$ (IFN-$\beta$), $\gamma$-interferon ($\gamma$-IFN), interleukin-1 (IL-1) in $\alpha$ and $\beta$ forms, interleukin-2 (IL-2), interleukin-3 (IL-3), interleukin-4 (IL-4), interleukin-5 (IL-5), interleukin-6 (IL-6), interleukin-10 (IL-10), interleukin-12 (IL-12), tumor necrosis factor (TNF) in $\alpha$ and $\beta$ forms, transforming growth factors (TGF-$\beta$), in $\beta$ 1, $\beta$ 2, $\beta$ 3, $\beta$ 1.2 forms, and colony-stimulating factors (CSF) such as the granulocyte macrophage-stimulating factor (GM-CSF), the granulocyte colony-stimulating factor (G-CSF) and the macrophage-stimulating factor (M-CSF) and the epithelial growth factor (EGF), somatostatin, endorphins, the various "releasing factors" or "inhibitory factors" such as TRF. There also exist pegilated forms of interferon. Cytokines play an essential role in the development of the immune system and thus in the development of an immune response. However, besides their numerous beneficial properties, they have also been implicated in the mechanisms for the development of a variety of inflammatory diseases. For example, the cytokines TNF-$\alpha$ and IL-1 are thought to be part of the disease causing mechanism of atherosclerosis, transplant arteriosclerosis, rheumatoid arthritis, lupus, scleroderma, emphysema, etc.

Important embodiments of the invention involve populations never before treated with a cytokine such as interferon. Thus, the invention involves, in certain aspects, treatments of individuals who are otherwise free of symptoms calling for treatment with interferons.

The cytokines and/or cobalamin compounds are preferably administered in effective amounts. In general, an effective amount is any amount that can cause an increase in Cbl-binding proteins activity in a desired cell population or tissue, and preferably in an amount sufficient to cause a favorable phenotypic change in the condition such as a lessening, alleviation or elimination of a symptom or of a condition.

With regard to the cobalamin or vitamin B derived compounds, an effective amount is that amount of a preparation that alone, or together with further doses, produces the desired response. This may involve only slowing the progression of the disease temporarily, although more preferably, it involves halting the progression of the disease permanently or delaying the onset of or preventing the disease or condition from occurring. This can be monitored by routine methods. Generally, doses of active compounds would be from about 0.01 mg/kg per day to 1000 mg/kg per day. It is expected that doses ranging from 50–500 mg/kg will be suitable, preferably intravenously, intramuscularly, or intradermally, and in one or several administrations per day.

Such amounts will depend, of course, on the particular condition being treated, the severity of the condition and the individual patient parameters. Some parameters for consideration include age, physical condition, size and weight, the duration of the treatment, the nature of concurrent therapy (if any), the specific route of administration and like factors within the knowledge and expertise of the health practitioner. Intravenous administration and intramuscular administration avoids transport problems associated with cobalamin when administered orally. However, if the vitamin $B_{12}$ analog, homolog or derivative is encapsulated, oral delivery may be preferred. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds. It is preferred generally that a maximum dose be used, that is, the highest safe dose according to sound medical judgment. Those of ordinary skill in the art will understand, however, that a patient may insist upon a lower dose or tolerable dose for medical reasons, psychological reasons or for virtually any other reason.

The cytokines (e.g. interferons) useful according to the invention may be combined, optionally, with a pharmaceutically-acceptable carrier. The term "pharmaceutically-acceptable carrier" as used herein means one or more compatible solid or liquid filters, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt. The pharmaceutical compositions also may contain, optionally, suitable preservatives, such as: benzalkonium chloride, chlorobutanol, parabens and thimerosal.

A variety of administration routes are available. The particular mode selected will depend, of course, upon the particular drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, intradermal, inhalation, intra-peritoneal, or parenteral routes. The term "parenteral" includes subcutaneous, intravenous, intramuscular, or infusion. Intravenous or intramuscular routes are particularly suitable for purposes of the present invention.

The pharmaceutical compositions may conveniently be presented in unit dosage form and may be prepared by any of the methods well known in the art of pharmacy. All methods include the step of bringing the active agent into association with a carrier that constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for parenteral administration conveniently comprise a sterile aqueous preparation of the cytokines and/or cobalamins, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1, 3-butane diol. Among the acceptable vehicles aid solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa. which is incorporated herein in its entirety by reference thereto.

Other delivery systems can include time-released, delayed release or sustained release delivery systems. Such systems can avoid repeated administrations of the active compound, increasing convenience to the subject and the physician, and may be particularly suitable for certain cobalamin drug conjugates of the present invention, particularly the nitrosyl-cobalamin due to its activation under acidic conditions found in the early gastrointestinal tract. Many types of release delivery systems are available and known to those of ordinary skill in the art. They include polymer base systems such as poly(lactide-glycolide), copolyoxalates, polycaprolactones, polyesteramides, polyorthoesters, poly-hydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di-and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active compound is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be desirable. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

In one aspect of the invention, the cytokine is "co-administered" with a metallocorrinoid which means administered substantially simultaneously with a metallocorrinoid. By substantially simultaneously, it is meant that the cytokine (e.g. interferon interferon-$\beta$) is administered to the subject close enough in time with the administration of the other agent (e.g., vitamin $B_{12}$ or a cobalamin conjugate), whereby the two compounds may exert an additive or even synergistic effect.

The following is provided as an illustration of the present invention as it applies to both in vivo and in vitro. The materials, methods, examples, results, and discussions should in no way be viewed as a limitation thereto. For simplicity, the materials and methods sections is provided after the following detailed discussion of the present invention.

Examples, Results and Discussion:

FIG. 1 illustrates NIH-OVCAR-3 ovarian carcinoma evaluated in accordance with the present invention after 72-hrs growth. Cytokines, particularly interferons, appear to enhance the activity or upregulate the cellular receptor for vitamin $B_{12}$ (TCII-R), resulting in enhanced TCII-R activity (in this case demonstrated by NO-Cbl uptake). Single agent and combination drug effects were assessed to determine whether IFN-$\beta$ enhanced NO-Cbl activity. As shown in FIG. 1, NIH-OVCAR-3 cells were treated continuously with varying concentrations of NO-Cbl and IFN-$\beta$. Consistent with our hypothesis, we observed synergistic anti-proliferative activity between IFN-$\beta$ and NO-Cbl. These matters are shown in the median effect analysis shown in FIG. 2 (similar to isobologram analysis) indicated synergy (a combination index <1) between NO-Cbl and IFN-$\beta$ at all 3 doses tested. Cytotoxicity was noted at the highest combination dose.

To assess the effect of IFN$\beta$ on TCII-R expression, a western blot analysis was performed on extracts from NIH-OVCAR-3 cells (ovarian carcinoma) as shown in FIG. 3. Lane 1 is untreated. Lanes 2 and 3 are IFN $\beta$ treated (200 u/ml) at 4 and 16 hrs respectively. Lanes 4 and 5 are liver and kidney extracts respectively, and serve as a positive control, since TCII-R is abundant in these tissues. As shown in FIG 3. IFN $\beta$ causes an increase in the expression of the TCII receptor, identified as the monomer at 62 kDa with the corresponding dimer at 124 kDa, consistent with TCII-R, These results correlate with the anti-proliferative effect of co-treatment of NIH-OVCAR-3 cells with IFN $\beta$ and nitrosylcobalamin shown in FIG. 1 The increased expression of the TCII receptor by IFN $\beta$ treatment results in the increased uptake of nitrosylcobalamin and thus enhanced destruction of the cells. The co-delivery of IFN-$\beta$ and nitrosylcobalamin appears to result in synergistic destruction of tumor cells as a result of increased TCII receptor expression or activity.

A flow cytometric analysis of Annexin V positive cells was performed to assess the % apoptosis (programmed cell death) of NIH-OVCAR-3 cells treated with NO-Cbl, alone and in combination with IFN-$\beta$. This is illustrated in FIG. 4 The $ID_{25}$ was used for both NO-Cbl (10 uM) and IFN-$\beta$ (20 U/mL) for 48 hrs. The effects of IL-2 (250 U/mL) were protective against the effects of NO-Cbl.

To further elucidate IFN-$\beta$ upregulated TCII-R, human NIH-OVCAR-3 tumors were grown in nude mice to a size of 3 mm in diameter. The control group received PBS and the treated group received human IFN-$\beta$ $10^5$ units daily for three days. Tumors were harvested, paraffin embedded, and sections were stained with rabbit polyclonal anti-TCII-R antibody, (provided by Dr. Seetharam's lab, Medical College of Wisconsin). FIG. 5 depicts these treatments. The left panel is an untreated tumor whereas the right panel is a tumor from a mouse that received IFN-$\beta$. The areas stained brown represent TCII-R. A comparison of the panels demonstrates increased expression of TCII-R with IFN $\beta$ treatment. The increased expression of the TCII receptor allows for increased uptake of NO-Cbl, consistent with the synergy observed in the SRB and Annexin V assays upon NO-Cbl co-treatment with IFN-$\beta$.

WM9 human melanoma was evaluated after 4 days growth. This is shown in FIG. 6. WM9 cells were treated continuously with varying concentrations of NO-Cbl and IFN-$\beta$. Similar to the NIH-OVCAR-3 cells, there was synergistic anti-proliferative activity between IFN-$\beta$ and NO-Cbl, as is shown in FIG. 7. Median effect analysis indicated synergy (a combination index <1) between NO-Cbl and IFN-$\beta$ at all 3 doses tested.

To further elucidate whether IFN-$\beta$ upregulated TCII-R, human WM9 tumors were grown in nude mice to a size of 3 mm in diameter. The control group received PBS and the treated group received human IFN-$\beta$ $10^5$ units daily for three days. Tumors were harvested, paraffin embedded, and sections were stained with rabbit polyclonal anti-TCII-R antibody, (provided by Dr. Seetharam's lab, Medical College of Wisconsin). FIG. 8 depicts these treatments. The upper two panels are untreated tumors whereas the lower panels are tumors from mice that received IFN-$\beta$. The areas stained brown represent TCII-R. A comparison of the panels demonstrates increased expression of TCII-R with IFN $\beta$ treatment.

One can see from the basal TCIIr activity in the NIH-OVCAR-3 and WM9 stained sections that when TCII-R expression is lower, NO-Cbl uptake is not pronounced. This is reflected by a higher $ID_{50}$ associated with the WM9 cells compared to NIH-OVCAR-3 and NIH-OVCAR-3 tumors. Although interferon administration in both NIH-OVCAR-3 and WM9 resulted in increased effectiveness of NO-Cbl, lower basal TCIIR expression in WM9 renders these cells less sensitive to the effect of NO-Cbl and the combination with IFN-$\beta$.

TCII-R is an important component of metallocorrinoid (e.g. vitamin $B_{12}$) metabolism and represents a site-specific target to regulate vitamin $B_{12}$ uptake. Nitrosylcobalamin, a vitamin $B_{12}$ based carrier of nitric oxide (NO), was used to validate the in vivo functional relevance of increased TCII-R expression. Intraperitoneal NO-Cbl treatment of established subcutaneous NIH-OVCAR-3 tumors resulted in tumor regression. The mean volume of untreated tumors was 18 fold greater compared to NO-Cbl treated tumors at the end of the study. Treated tumors decreased 4-fold in volume during the treatment period. There was no histologic evidence of toxicity to normal tissues at NO-Cbl doses of 170 mg/kg/day after 60 days. IFN-β treatment of NIH-OVCAR-3 cells in culture resulted in increased expression of the TCII-R, detected as a monomer (62 kDa) and a dimer (124 kDa). Similarly, immunohistochemical analysis of NIH-OVCAR-3 xenografts from nude mice that received human IFN-β showed increased TCII-R expression compared to controls. Tumors that were resistant to IFN-β and NO-Cbl in vivo exhibited minimal to no immunohistochemical evidence of TCII-R upregulation. In culture, combination treatment with IFN-β and NO-Cbl resulted in synergistic anti-proliferative activity in NIH-OVCAR-3 cells and several different human cells lines including MCF-7 (breast), DU145 and LNCap (prostate), ACHN (renal), A549 (lung), WM9, WM35, WM164, and WM3211 (melanoma). Treatment of NIH-OVCAR-3 cells with the combination of NO-Cbl and IFN-β resulted in a 2-fold increase in annexin V positive cells compared to NO-Cbl alone. Interestingly, a Ribonucleotide Protection Assay revealed a ten-fold increase in TRAIL and Caspase 7 in NIH-OVCAR-3 cells treated with the combination of NO-Cbl and IFN-β. Therefore, up-regulation and/or increased activity of the TCII-R by IFN-β results in synergistic anti-tumor effects in vitro and in vivo.

Materials and Methods:

In-vivo IFN-β treatment of nude mice inoculated with tumors (e.g. WM9—human melanoma or NIH-OVCAR-3—ovarian carcinoma) and Immunohistochemical analysis: Nude mice (n=2 each group), were inoculated with tumors (e.g. WM9—human melanoma or NIH-OVCAR-3—ovarian carcinoma), subcutaneously (s.c.), one tumor on each flank. The tumors were grown until 3–5 mm in diameter. Human IFN-β ($10^5$ units) was administered s.c. for three days to the treatment animals. On day four, animals were sacrificed and tumors were fixed in formalin and paraffin embedded. The sections were analyzed using standard immunohistochemical techniques. Anti-TCII-R was used as the primary antibody.

SRB Anti-Proliferative Cell Survival Assay:

Cells ($2\times10^3$) were seeded in 96-well plates. Data points represent mean of eight replicates. (n=8). A control plate was fixed 4 hr after seeding (to allow cells to attach) to determine the initial seeding density ($A_{ini}$). This was defined as 0% growth. To the wells of the seeded experimental plate, IFN-β was added and incubation continued for 3–5 days. Untreated cell controls were included. Growth obtained with this control was defined as 100% ($A_{fin}$). To determine cell number, cells were fixed with 10% trichloroacetic acid at 4° C. for 1 h. They were stained with 0.4% sulforhodamine B prepared in 1% acetic acid at 25° C. for 1 h (27). The wells were washed with 1% acetic acid. Bound dye was eluted with 100 μl of 10 mM Tris-HCl, ph 10.5 and quantitated in a microplate reader at 570 nm. Growth in IFN-β-treated wells (experimental=exp) was expressed as a percentage of untreated control growth (mean±SEM).

%Control growth=100%×$(A_{exp}-A_{ini})/(A_{fin}-A_{ini})$

%STD=100%×$(STD_{exp}/(A_{fin}-A_{ini}))$

%SEM=100%×$(SEM_{exp}/(A_{fin}-A_{ini}))$ where SEM=STD/$\sqrt{n}$

Western Blot TCII Receptor:

Cells in culture were treated with vehicle (untreated) or with IFN-β (500 U/ml) for 4 and 16 hrs, washed twice in PBS, harvested by scraping, and lysed in buffer containing 100 mM saline-TRIS. Total cell extracts were homogenized prior to loading. Protein amounts in clarified cell extracts were determined using Bio-Rad protein assay reagent. Equivalent amounts of protein (100 μg) were loaded on 10% polyacrylamide SDS separating gels and electrophoresis was performed using glycine-SDS buffer. Following electrophoresis, gels were equilibrated in transfer buffer 30 min at 25° C., and proteins transferred to nitrocellulose membrane.

Immunoblot with Electro-Chemiluminescense Detection:

All steps were performed at 25° C. Following 90 min electrophoretic wet transfer, the membranes were incubated in washing buffer TBS-Tween (1×TBS, 0.2% X-100,)+4% BSA for 1–2 hr to block non-specific binding. The membrane was washed in washing buffer. Membranes were then incubated in 25 ml of primary antibody at 1:500 dilution in the washing buffer overnight at 4° C. Membranes were then washed using the washing buffer four times, 10 min each Membranes were incubated in 50 ml horseradish peroxidase-conjugated secondary antibody (Zymed) at 1:10,000 dilution in washing buffer for 30 minutes. Membranes were washed in the washing buffer for two hours. Equal volumes of electro-chemiluminescense (ECL) reagents A and B (Amersham) were mixed to give enough reagents to develop the blot (0.125 ml/cm$^2$). Excess buffer was drained from the membrane and it was placed protein side up on plastic wrap. Detection reagent was added to the protein side of the membrane. The reaction was allowed to continue for exactly 1 minute. Excess detection reagent was drained and the membrane was placed protein side down on plastic wrap and exposed to film for empirically determined lengths of time.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods, and in the steps or in the sequence of steps of the method described herein, without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The following references, to the extent that they provide exemplary procedural or other details supplementary to those set forth herein, are specifically incorporated herein by reference:

McLean G R, Williams M J, Woodhouse C S, Ziltener H J: Transcobalamin II and in vitro proliferation of leukemic cells. Leuk Lymphoma 30: 101–9, 1998.

Tsao C S, Myashita K: Influence of cobalamin on the survival of mice bearing ascites tumor. Pathobiology 61: 104–8, 1993.

Jensen H S, Gimsing P, Pedersen F, Hippe E: Transcobalamin II as an indicator of activity in metastatic renal adenocarcinoma. Cancer 52: 1700–4, 1983.

Tsao C S, Miyashita K, Young M: Cytotoxic activity of cobalamin in cultured malignant and nonmalignant cells. Pathobiology 58: 292–6, 1990.

Shimizu N, Hamazoe R, Kanayama H, Maeta M, Koga S: Experimental study of antitumor effect of methyl-B12. Oncology 44: 169–73, 1987.

McLean G R, Pathare P M, Wilbur D S, Morgan A C, Woodhouse C S, Schrader J W, Ziltener H J: Cobalamin analogues modulate the growth of leukemia cells in vitro. Cancer Res 57: 4015–22, 1997.

Huennekens F M, DiGirolamo P M, Fujii K, Jacobsen D W, Vitols K S: B12—dependent methionine synthetase as a potential target for cancer chemotherapy. Adv Enzyme Regul 14: 187–205, 1976.

Bauer, Joseph A., Characterization and nitric oxide release profile of nitrosylcobalamin: a potential chemotherapeutic agent. Anti-Cancer Drugs 1998; 9(3): 239–244.

What is claimed is:

1. A therapeutic composition comprising a cobalamin drug conjugate and interferon-β.

2. The therapeutic composition of claim 1, wherein said cobalamin drug conjugate is a radiolabeled Vitamin $B_{12}$ analog.

3. The therapeutic composition of claim 1, wherein said cobalamin drug conjugate is nitrosylcobalamin.

4. The therapeutic composition of claim 1, further including a pharmaceutical carrier.

5. A method of enhancing uptake of a cobalamin drug conjugate comprised of administering interferon-β in an amount effective to enhance uptake of the cobalamin drug conjugate and then administering the cobalamin drug conjugate.

6. The method of claim 5, wherein said cobalamin drug conjugate is a radiolabeled Vitamin $B_{12}$ analog.

7. The method of claim 5, wherein said cobalamin drug conjugate is nitrosylcobalamin.

8. A method of treating a patient in need thereof comprising the steps of inducing interferon-β production and then administering a cobalamin drug conjugate.

9. The method of claim 8, wherein the step of inducing interferon-β production comprises administering interferon-β.

10. The method of claim 8, wherein said cobalamin drug conjugate is radiolabeled Vitamin $B_{12}$.

11. The method of claim 8, wherein said cobalamin drug conjugate is nitrosylcobalamin.

12. A method for increasing TCII-R activity in a subject to treat, ameliorate, or diagnose a condition characterized by cellular proliferation comprising the step of administering to a subject in need of such treatment interferon-β in and amount effective to increase TCII-R activity in the subject and administering a cobalamin drug conjugate.

13. The method of claim 12, comprising the step of co-administering the cobalamin drug conjugate.

14. The method of claim 12, wherein said interferon-β is administered prophylactically.

15. The method of claim 12, wherein said interferon-β is administered acutely.

16. The method of claim 12, wherein said cytokine is administered acutely.

17. The method of claim 12, wherein said condition is unwanted cellular proliferation.

18. A method of enhancing bio-availability of a cobalamin drug conjugate comprising the steps of administering interferon-β and the cobalamin drug conjugate.

19. The method of claim 18, wherein the cobalamin drug conjugate is nitrosylcobalamin.

20. The method of claim 18, wherein the cobalamin drug conjugate is administered prior to said interferon-β.

21. The method of claim 18, wherein the cobalamin drug conjugate is administered simultaneously with said interferon-β.

22. The method of claim 18, wherein the cobalamin drug conjugate is administered after said interferon-β.

23. A method of treating a subject comprising the steps of first administering to a subject in need thereof interferon-β in an amount effective to increase TCII-R activity in a cell and administering a ligand cobalamin drug conjugate.

24. The method of claim 23, wherein the subject is cobalamin deficient.

25. The method of claim 23, wherein the amount is sufficient to increase TCII-R activity above normal baseline levels.

26. The method of claim 23, wherein the subject has an abnormally low level of TCII-R activity.

27. The method of claim 23 wherein the cobalamin drug conjugate is nitrosylcobalamin.

28. The method of claim 23, wherein the cobalamin drug conjugate is radiolabelled Vitamin $B_{12}$.

* * * * *